US00PP26837P2

(12) United States Plant Patent
Bradford et al.

(10) Patent No.: US PP26,837 P2
(45) Date of Patent: Jun. 21, 2016

(54) NECTARINE TREE NAMED 'KAY DIAMOND VIII'

(50) Latin Name: *Prunus persica*
Varietal Denomination: Kay Diamond VIII

(71) Applicants: Lowell Glen Bradford, Le Grand, CA (US); Jon M. Quisenberry, Le Grand, CA (US)

(72) Inventors: Lowell Glen Bradford, Le Grand, CA (US); Jon M. Quisenberry, Le Grand, CA (US)

( * ) Notice: Subject to any disclaimer, the term of this patent is extended or adjusted under 35 U.S.C. 154(b) by 38 days.

(21) Appl. No.: 14/544,250

(22) Filed: Dec. 15, 2014

(51) Int. Cl.
*A01H 5/08* (2006.01)

(52) U.S. Cl.
USPC ..... Plt./190

(58) Field of Classification Search
USPC ..... Plt./190
CPC ..... A01H 5/0856; A01H 5/0837
See application file for complete search history.

(56) References Cited

U.S. PATENT DOCUMENTS

PP16,494 P2 5/2006 Bradford
PP18,715 P2 4/2008 Bradford

*Primary Examiner* — Kent L Bell

(57) ABSTRACT

The present invention relates to a new and distinct variety of nectarine tree, *Prunus persica*, broadly characterized by a medium size, vigorous, hardy, self-fertile, productive and regular bearing tree. The variety blooms during the early to mid-season and requires about 500 chilling hours. The fruit matures under the ecological conditions described in late May, with first picking on May 27, 2014. The fruit is uniformly medium to large in size, globose in shape, acidic and sweet in flavor, clingstone in type, firm and melting in texture, yellow in flesh color, and nearly full red in skin color.

1 Drawing Sheet

Botanical classification: *Prunus persica.*
Variety denomination: 'KAY DIAMOND VIII'.

BACKGROUND OF THE VARIETY

In a continuing effort to improve the quality of shipping fruits, we, the inventors, typically hybridize a large number of peach, nectarine, plum, apricot, and cherry seedlings each year. We also grow a lesser number of open pollinated seeds of each of these fruits, usually to capture recessive traits. The present invention relates to a new and distinct variety of nectarine tree, which has been denominated varietally as 'Kay Diamond VIII'.

The present variety was hybridized by us in 2007 as a first generation cross using 'Grand Bright' (U.S. Plant Pat. No. 16,494) nectarine as the selected seed parent and 'Kay Diamond VII' (U.S. Plant Pat. No. 18,715) nectarine as the selected pollen parent. The fruit of this cross was gathered in the summer of 2007, and the seeds were removed from the fruit, cracked, stratified, germinated, and grown as seedlings on their own root in our greenhouse. Upon reaching dormancy the seedlings were transplanted as a group to a cultivated area of our experimental orchard located near Le Grand, Calif., in Merced County (San Joaquin Valley). During the fruit evaluation season of 2011 we selected the present variety as a single tree from the group of seedlings described above. Subsequent to origination of the present variety of nectarine tree, we asexually reproduced it by budding and grafting in the experimental orchard described above, and such reproductions were true to the original tree in all respects. The reproduction of the variety included the use of 'Nemaguard' (unpatented) rootstock upon which the present variety was compatible and true to type.

The present variety is similar to its seed parent, 'Grand Bright' (U.S. Plant Pat. No. 16,494) nectarine by having showy blossoms, by being self-fertile, and by producing nectarines that are nearly full red in skin color, yellow in flesh color, firm in texture, globose in shape, clingstone in type, and very good in flavor, but is distinguished therefrom by having globose instead of reniform leaf glands and by producing fruit that is somewhat smaller in size, that has a bitter kernel instead of sweet, and that matures about thirty days earlier.

The present variety is most similar to its pollen parent, 'Kay Diamond VII' (U.S. Plant Pat. No. 18,715) nectarine by being self-fertile, by having showy blossoms, by requiring about 500 chilling hours, and by producing nectarines that are nearly full red in skin color, yellow in flesh color, firm in texture, globose in shape, clingstone in type, very good in flavor, and medium to large in size for the early season, but is distinguished therefrom by having globose leaf glands instead of being eglandular, by blooming about 6 days later, and by producing fruit that matures about ten days later.

SUMMARY OF VARIETY

In summary, the present nectarine tree variety is characterized by a medium size, vigorous, hardy, self-fertile, productive and regular bearing tree. The variety blooms during the early to mid-season and requires about 500 chilling hours. The fruit matures under the ecological conditions described in late May, with first picking on May 27, 2014. The fruit is uniformly medium to large in size, globose in shape, acidic and sweet in flavor, clingstone in type, firm and melting in texture, yellow in flesh color, and nearly full red in skin color.

DRAWING

The accompanying photograph consists of four whole fruits positioned to display the characteristics of the skin color and form, one divided fruit to reveal the flesh and stone, two insets to reveal buds and a blossom, and characteristic leaves.

POMOLOGICAL CHARACTERISTICS

Referring now more specifically to the pomological characteristics of this new and distinct variety of nectarine tree, the following has been observed under the ecological conditions prevailing near Le Grand, Merced County (San Joaquin Valley), Calif., and was developed at the state of firm ripe on May 30, 2014, on the original tree during its seventh growing season. The blossom and flower descriptions were made the previous blooming season. All major color code designations are by reference to the Inter-Society Color Council, National Bureau of Standards. Common color names are also used occasionally.

It is to be noted that 2014 was an abnormal year with drought conditions existing in California. The unusually clear, warm, and dry weather in January led to a very low amount of acquired chilling units, an earlier than normal blooming season, and an earlier than normal ripening season for the entire spring and summer.

PARENTAGE

Seed parent: 'Grand Bright' (U.S. Plant Pat. No. 16,494) nectarine.

Pollen parent: 'Kay Diamond VII' (U.S. Plant Pat. No. 18,715) nectarine.

TREE

Size: Medium, reaching and maintaining a height of 12' [3.66 m.] and a spread of 6' [1.83 m.] after seven growing seasons utilizing typical dormant pruning.

Vigor: Vigorous, responding typically to irrigation and fertilization. The variety grows about 3' [0.91 m.] of surplus top-growth during the spring and summer. The plant should be grown on a standard commercial rootstock for production purposes.

Growth: Spreading and dense.

Form: Vase formed.

Hardiness: Hardy with respect to central California winters.

Heat tolerance: Observed to perform adequately in typical central California climatic conditions, which typically include extended periods of heat.

Drought tolerance: Variety is developed for commercial orchards and requires regular irrigation.

Production: Productive.

Fertility: Self-fertile.

Bearing: Regular bearer with no alternate bearing yet observed.

Approximate chilling requirement: 500 hours.

Trunk:

- *Size*.—Medium, reaching a maximum diameter of 4¼" [108 mm.] after the seventh growing season.
- *Texture*.—Medium shaggy.
- *Bark color*.—A Grayish brown [61. gy.Br] and Dark grayish reddish brown [47. d.gy.rBr] variegation.
- *Lenticels*.—Approximate Number Per Square Inch: 9. Color: Brownish orange [54. brO]. Average Size: 5/16" [7.9 mm.] in length and 1/16" [1.6 mm.] in width. Shape: Eye-shaped, elongated.

Branches:

- *Size*.—Diameter of limb is 2¾" [69.9 mm.] measured 12" above the crotch, 2" [50.8 mm.] measured 12" above the first fork.
- *Texture*.—Medium smooth on first year wood, increasing roughness with age.
- *Color*.—1st Year Wood Topside: Grayish red [19. gy.R]. 1st Year Wood Underside: Brilliant yellow green [116. brill.YG]. Second Year and Older Wood: Strong yellowish brown [74. s.yBr].
- *Lenticels*.—Number Per Square Inch: About 120 on second year wood. Color: Moderate orange yellow [71. m.OY]. Average size: 1/16" [1.6 mm.] in length and 1/64" [0.4 mm.] in width on second year wood. Shape: Eye-shaped, elongated.

Leaves:

- *Size*.—Large.
- *Average length*.—5⅞" [149.2 mm.].
- *Average width*.—1¾" [44.5 mm.].
- *Arrangement*.—Alternate.
- *Thickness*.—Medium.
- *Form*.—Elliptical.
- *Apex*.—Acuminate.
- *Base*.—Acute, with an average base angle of 75 degrees.
- *Surface*.—Smooth.
- *Color*.—Dorsal Surface: Moderate olive green [125. m.OlG]. Ventral Surface: Moderate yellow green [120. m.YG].
- *Margin*.—Finely serrate.
- *Venation*.—Pinnately net veined.
- *Vein color*.—Light yellow green [119. l.YG].
- *Petiole*.—Average Length: 7/16" [11.1 mm.]. Average Thickness: 1/16" [1.6 mm.]. Color: Brilliant yellow green [116. brill.YG].
- *Stipules*.—Number: Usually 2 per leaf, up to 6 per growing tip. Average Length: ¼" [6.4 mm.]. Color: Moderate yellow green [120. m.YG] becoming Dark reddish brown [44. d.rBr] with maturity.
- *Glands*.—Number: 2 to 4 per leaf. Position: Mostly alternate on petiole and base of blade. Size: Small, about 1/48" [0.5 mm.] in diameter. Form: Globose. Color: Moderate yellow green [120. m.YG] becoming Dark yellowish brown [78. d.yBr] with age.
- *Leaf buds*.—Pointed, medium in size.

Flower buds:

- *Hardiness*.—Hardy, with respect to central California winters.
- *Diameter*.—Typically ⅜" [9.5 mm.] 1 week before bloom.
- *Length*.—Typically ⅝" [15.9 mm.] 1 week before bloom.
- *Form*.—Not appressed.
- *Surface*.—Pubescent.
- *Tip color*.—Light purplish pink [249. l.pPk].

Flowers: Perfect, complete, perigynous, usually a single pistil, about thirty stamens, five sepal and petal locations alternately positioned.

- *Type*.—Showy, large.
- *Average flower diameter*.—2" [50.8 mm.].
- *Average flower depth*.—7/16" [11.1 mm.] when fully open.
- *Number of petals*.—Always five full petals with about thirty percent having extra petals or petal fragments, full double blossoms occur rarely.
- *Petal shape*.—Circular to oval.

*Petal margin*.—Entire, wavy with a few notches.
*Average petal diameter*.—11/16" [17.5 mm.].
*Average petal length*.—3/4" [19.1 mm.].
*Petal apex*.—Rounded.
*Petal base*.—Rounded to truncate.
*Petal color*.—Light pink [4. l.Pk] toward the apex, Moderate pink [5. m.Pk] toward the base on both sides.
*Anther color*.—Deep red [13. deep R] over a Light yellow [86. l.Y] center at bloom onset.
*Pollen*.—Anthers produce an abundance of Brilliant yellow [83. brill.Y] pollen.
*Stigma color*.—Light greenish yellow [101. l.gY].
*Stigma position*.—Typically located about even with nearby anthers.
*Ovary*.—Non-pubescent.
*Sepal color*.—Dark purplish red [259. d.pR] on the outer surface. The inner surface is a somewhat translucent Pinkish white [9. pkWhite] with both Grayish purplish red [262. gy.pR] and Vivid yellow green [115. v.YG] areas visible.
*Sepal length*.—1/4" [6.4 mm.].
*Sepal width*.—3/16" [4.8 mm.].
*Sepal apex*.—Rounded to elliptical to match the sepal length and width.
*Sepal margin*.—Fairly smooth.
*Average pistil length*.—11/16" [17.5 mm.].
*Average stamen length*.—9/16" [14.3 mm.].
*Fragrance*.—Moderate.
*Blooming period*.—Early to medium, blooms at the same time as 'Rose Bright' (U.S. Plant Pat. No. 15,845) nectarine.
*Onset of bloom*.—One percent on Feb. 15, 2014.
*Date of full bloom*.—Feb. 23, 2014.
*Duration of bloom*.—One to two weeks, dependent on ambient temperature.
*Number per cluster*.—1 to 3 with single flowers most common.

FRUIT

Maturity when described: Firm ripe, May 30, 2014.
Date of first picking: May 27, 2014.
Date of last picking: Jun. 6, 2014.
Size: Uniform, medium to large.
*Average diameter axially*.—2 15/16" [74.6 mm.].
*Average diameter across cheek plane*.—2 7/8" [73 mm.].
*Average diameter across suture plane*.—3" [76.2 mm.].
*Typical weight*.—7.9 ounces [224 grams].
Form: Mostly uniform, globose, symmetrical.
*Longitudinal section form*.—Round to elliptical.
*Axial view*.—Round.
Suture: Extends from the base, along the side, and ends just past the pistil point.
*Near the base*.—A shallow groove.
*Along the side*.—A shallow trough.
*Near the apex*.—A shallow groove.
Ventral surface: Rounded, lipped throughout, but stronger toward the apex.
Lips: Fairly equal.
Cavity: Flaring, slightly elongated in the suture plane, suture showing on one side, Brilliant greenish yellow [98. brill.gY] stem markings typical.
*Depth*.—1/2" [12.7 mm.].
*Breadth*.—7/8" [22.2 mm.].
Base: Rounded, but appears cordate if viewed parallel to the suture.
Apex: Rounded, but appears cordate if viewed parallel to the suture.
Pistil point: Apical, negligible in length, depressed within the suture.
Stem: Medium.
*Average length*.—3/8" [9.5 mm.].
*Average width*.—3/16" [4.8 mm.].
Skin:
*Thickness*.—Medium.
*Surface*.—Smooth.
*Tenacity*.—Tenacious to flesh.
*Astringency*.—Moderately acidic.
*Tendency to crack*.—None observed in dry season.
*Color*.—Very deep red [14. v.deep R] smoothly blending into Deep red [13. deep R] over a background of Moderate orange yellow [71. m.OY] with moderate Light orange yellow [70. l.OY] freckling toward the apex.
Flesh:
*Color*.—Brilliant yellow [83. brill.Y] with virtually no red streaking or bleeding.
*Surface of pit cavity*.—Covered with Deep orange yellow [69. deep OY] broken fibers when twisted from the stone.
*Amygdalin*.—Scarce.
*Juice*.—Moderate, rich and watery.
*Texture*.—Firm, crisp, melting.
*Fibers*.—Abundant, fine.
*Ripens*.—Slightly earlier at the apex.
*Flavor*.—Acidic and sweet, typically 14 brix.
*Aroma*.—Moderate.
*Eating quality*.—Very good, a nice blend of acid and sugar with traditional nectarine flavor.

STONE

Type: Clingstone.
Form: Oval.
Hilum: Narrow, oblong.
Base: Truncate.
Apex: Obtuse with an average angle of 105 degrees.
Sides: Equal.
Surface: Irregularly furrowed and ridged toward the apex, pitted toward base.
Ridges: Jagged.
External color: Dark orange yellow [72. d.OY].
Pit wall color when cracked: Light yellowish brown [76. l.yBr].
Cavity surface color: A Deep brown [56. deep Br] and Light yellowish brown [76. l.yBr] two-tone.
Average pit wall thickness: 1/4" [6.4 mm.].
Average width: 1 1/8" [28.6 mm.].
Average length: 1 7/16" [36.5 mm.].
Average breadth: 3/4" [19.1 mm.].
Tendency to split: Slight.
Kernel:
*Form*.—Oval.
*Skin color*.—Brilliant yellow [83. brill.Y] when first removed.
*Pellicle color*.—Moderate brown [58. m.Br].
*Vein color*.—Strong brown [55. s.Br].
*Taste*.—Bitter.
*Viable*.—Yes.

*Average width.*—7/16" [11.1 mm.].
*Average length.*—¾" [19.1 mm.].
*Amygdalin.*—Abundant.

USE

Market: Fresh market and long distance shipping.
Keeping quality: Good. Fruit quality observed to remain in good condition after 21 days in standard cold room at 36° Fahrenheit [2° Celsius].
Shipping quality: Good.
Resistance to insects: No unusual susceptibilities noted.
Resistance to diseases: No unusual susceptibilities noted.

OTHER NOTES

Although the new variety of nectarine tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

We claim:

1. A new and distinct variety of nectarine tree, substantially as illustrated and described, that is most similar to its pollen parent, 'Kay Diamond VII' (U.S. Plant Pat. No. 18,715) nectarine by being self-fertile, by having showy blossoms, by requiring about 500 chilling hours, and by producing nectarines that are nearly full red in skin color, yellow in flesh color, firm in texture, globose in shape, clingstone in type, very good in flavor, and medium to large in size for the early season, but is distinguished therefrom by having globose leaf glands instead of being eglandular, by blooming about 6 days later, and by producing fruit that matures about ten days later.

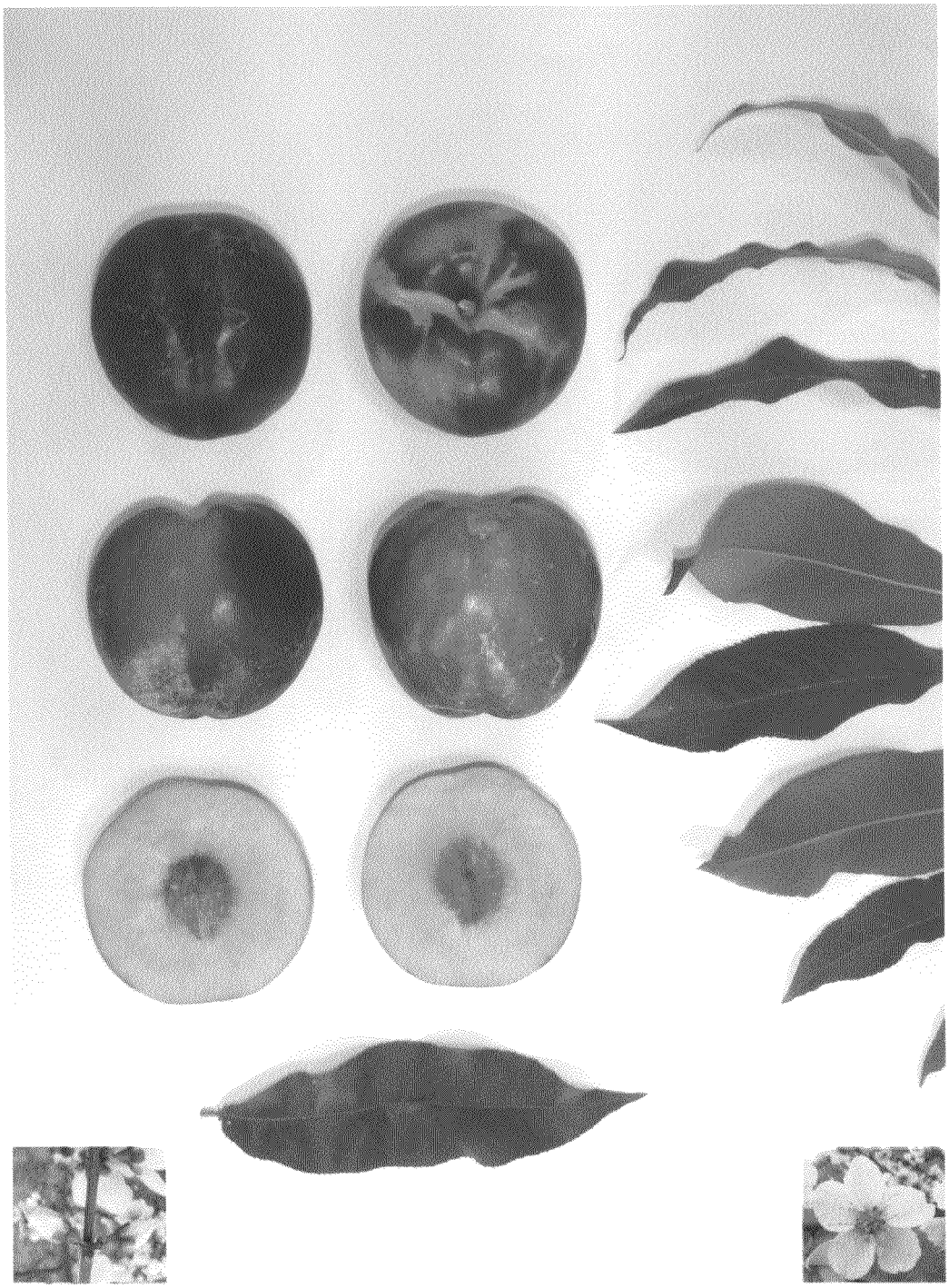

* * * * *